(12) United States Patent
Ellison et al.

(10) Patent No.: US 7,024,316 B1
(45) Date of Patent: Apr. 4, 2006

(54) TRANSIENTLY DYNAMIC FLOW CYTOMETER ANALYSIS SYSTEM

(75) Inventors: Carl E. Ellison, Fort Collins, CO (US); Paul Barclay Purcell, Ouray, CO (US); George C. Malachowski, Fort Collins, CO (US); Matthias J. Ottenberg, Fort Collins, CO (US)

(73) Assignee: DakoCytomation Colorado, Inc., Fort Collins, CO (US)

( * ) Notice: Subject to any disclaimer, the term of this patent is extended or adjusted under 35 U.S.C. 154(b) by 347 days.

(21) Appl. No.: 10/111,026

(22) PCT Filed: Oct. 20, 2000

(86) PCT No.: PCT/US00/41372

§ 371 (c)(1),
(2), (4) Date: Apr. 18, 2002

(87) PCT Pub. No.: WO01/28700

PCT Pub. Date: Apr. 26, 2001

Related U.S. Application Data (60) Provisional application No. 60/160,719, filed on Oct. 21, 1999.

(51) Int. Cl.
*G06F 17/00* (2006.01)

(52) U.S. Cl. ............................ 702/45; 702/21; 702/25; 702/32; 702/50; 422/68.1; 422/73

(58) Field of Classification Search ............ 702/45, 702/21, 29, 22, 23, 25–28, 30–32, 49, 50, 702/55, 57, 85, 100, 104, 127, 128, 179, 702/183, 189, 198; 209/3.1, 364, 3, 576, 209/579, 906; 700/266, 271, 273, 281, 282, 700/285; 377/21; 436/50, 17, 10; 356/39, 356/72; 422/50, 62, 67, 68.1, 73; 73/863.21, 73/863.22, 865.5, 861.39, 861.41, 861.02, 73/861.03, 861.04

See application file for complete search history.

(56) References Cited

U.S. PATENT DOCUMENTS

| 3,299,354 A | 1/1967 | Hogg ......................... 207/582 |
| 3,661,460 A | 5/1972 | Elking et al. ................. 356/36 |

(Continued)

FOREIGN PATENT DOCUMENTS

| DE | 19549015 | 3/1997 | ................... 21/85 |

(Continued)

OTHER PUBLICATIONS

Axicon; Journal of the Optical Society of America; vol. 44, #8, Eastman Kodak Company, Hawk-Eye Works, Rochester, NY, Sep. 10, 1953, pp. 592-597.

(Continued)

*Primary Examiner*—Hal Wachsman
(74) *Attorney, Agent, or Firm*—Santangelo Law Offices, P.C.

(57) ABSTRACT

A flow cytometry apparatus and methods to process information incident to particles or cells entrained in a sheath fluid stream allowing assessment, differentiation, assignment, and separation of such particles or cells even at high rates of speed. A first signal processor individually or in combination with at least one additional signal processor for applying compensation transformation on data from a signal. Compensation transformation can involve complex operations on data from at least one signal to compensate for one or numerous operating parameters. Compensated parameters can be returned to the first signal processor for provide information upon which to define and differentiate particles from one another.

136 Claims, 2 Drawing Sheets

U.S. PATENT DOCUMENTS

| Patent | Date | Inventor | Class |
|---|---|---|---|
| 3,710,933 A | 1/1973 | Fulwyler et al. | 209/3 |
| 3,761,941 A | 9/1973 | Robertson | 346/1 |
| 3,810,010 A | 5/1974 | Thom | 324/71 |
| 3,826,364 A | 7/1974 | Bonner et al. | 209/3 |
| 3,833,796 A | 9/1974 | Fetner et al. | 235/151.3 |
| 3,960,449 A | 6/1976 | Carleton et al. | 356/103 |
| 3,963,606 A | 6/1976 | Hogg | 209/3 |
| 3,973,196 A | 8/1976 | Hogg | 324/71 |
| 4,014,611 A | 3/1977 | Simpson et al. | 356/72 |
| 4,070,617 A | 1/1978 | Kachel et al. | 324/71 |
| 4,074,809 A | 2/1978 | McMillin et al. | 209/588 |
| 4,162,282 A | 7/1979 | Fulwyler et al. | 264/9 |
| 4,230,558 A | 10/1980 | Fulwyler | 209/3.1 |
| 4,302,166 A | 11/1981 | Fulwyler et al. | 425/6 |
| 4,317,520 A | 3/1982 | Lombardo et al. | 209/3.1 |
| 4,318,480 A | 3/1982 | Lombardo et al. | 209/3.1 |
| 4,318,481 A | 3/1982 | Lombardo et al. | 209/3.1 |
| 4,318,482 A | 3/1982 | Barry et al. | 209/3.1 |
| 4,318,483 A | 3/1982 | Lombardo et al. | 209/3.1 |
| 4,325,483 A | 4/1982 | Lombardo et al. | 209/3.1 |
| 4,341,471 A | 7/1982 | Hogg et al. | 356/343 |
| 4,350,410 A | 9/1982 | Minott | 350/170 |
| 4,361,400 A | 11/1982 | Gray et al. | 356/23 |
| 4,395,676 A | 7/1983 | Hollinger et al. | 324/71.4 |
| 4,400,764 A | 8/1983 | Kenyon | 362/263 |
| 4,487,320 A | 12/1984 | Auer | 209/3.1 |
| 4,498,766 A | 2/1985 | Unterleitner | 356/73 |
| 4,501,336 A | 2/1985 | Kemp et al. | 175/61 |
| 4,515,274 A | 5/1985 | Hollinger et al. | 209/3.1 |
| 4,523,809 A | 6/1985 | Toboada et al. | 350/163 |
| 4,538,733 A | 9/1985 | Hoffman | 209/3.1 |
| 4,598,408 A | 7/1986 | O'Keefe | 372/94 |
| 4,600,302 A | 7/1986 | Sage, Jr. | 356/39 |
| 4,631,483 A | 12/1986 | Proni et al. | 324/71.4 |
| 4,673,288 A | 6/1987 | Thomas et al. | 356/72 |
| 4,691,829 A | 9/1987 | Auer | 209/3.1 |
| 4,702,598 A | 10/1987 | Böhmer | 356/343 |
| 4,744,090 A | 5/1988 | Freiberg | 372/94 |
| 4,758,729 A | 7/1988 | Monnin | 250/560 |
| 4,794,086 A | 12/1988 | Kasper et al. | 436/36 |
| 4,818,103 A | 4/1989 | Thomas et al. | 356/72 |
| 4,831,385 A | 5/1989 | Archer et al. | 346/1.1 |
| 4,845,025 A | 7/1989 | Lary et al. | 435/2 |
| 4,877,965 A | 10/1989 | Dandliker et al. | 250/458.1 |
| 4,942,305 A | 7/1990 | Sommer | 250/574 |
| 4,981,580 A | 1/1991 | Auer | 209/3.1 |
| 4,983,038 A | 1/1991 | Ohki et al. | 356/246 |
| 4,987,539 A | 1/1991 | Moore et al. | 364/413.08 |
| 5,005,981 A | 4/1991 | Schulte et al. | 366/219 |
| 5,007,732 A | 4/1991 | Ohki et al. | 356/73 |
| 5,030,002 A | 7/1991 | North, Jr. | 356/73 |
| 5,034,613 A | 7/1991 | Denk et al. | 250/458.1 |
| 5,079,959 A | 1/1992 | Miyake et al. | 73/864.85 |
| 5,098,657 A | 3/1992 | Blackford et al. | 422/73 |
| 5,101,978 A | 4/1992 | Marcus | 209/3.1 |
| 5,127,729 A | 7/1992 | Oetliker et al. | 356/317 |
| 5,135,759 A | 8/1992 | Johnson | 424/561 |
| 5,144,224 A | 9/1992 | Larsen | 324/71.4 |
| 5,150,313 A | 9/1992 | Van den Engh et al. | 364/569 |
| 5,159,397 A | 10/1992 | Kosaka et al. | 356/73 |
| 5,159,403 A | 10/1992 | Kosaka | 356/243 |
| 5,167,926 A | 12/1992 | Kimura et al. | 422/67 |
| 5,180,065 A | 1/1993 | Touge et al. | 209/577 |
| 5,182,617 A | 1/1993 | Yoneyama et al. | 356/440 |
| 5,199,576 A | 4/1993 | Corio et al. | 209/564 |
| 5,215,376 A | 6/1993 | Schulte et al. | 366/348 |
| 5,247,339 A | 9/1993 | Ogino | 356/73 |
| 5,259,593 A | 11/1993 | Orme et al. | 266/78 |
| 5,260,764 A | 11/1993 | Fukuda et al. | 356/73 |
| 5,298,967 A | 3/1994 | Wells | 356/336 |
| 5,359,907 A | 11/1994 | Baker et al. | 73/865.5 |
| 5,367,474 A | 11/1994 | Auer et al. | 364/555 |
| 5,370,842 A | 12/1994 | Miyazaki et al. | 422/82.06 |
| 5,412,466 A | 5/1995 | Ogino | 356/246 |
| 5,452,054 A | 9/1995 | Dewa et al. | 355/67 |
| 5,466,572 A | 11/1995 | Sasaki et al. | 435/2 |
| 5,467,189 A | 11/1995 | Kreikebaum et al. | 356/336 |
| 5,483,469 A | 1/1996 | Van den Engh et al. | 364/555 |
| 5,503,994 A | 4/1996 | Shear et al. | 436/90 |
| 5,523,573 A | 6/1996 | Hänninen et al. | 250/459.1 |
| 5,558,998 A | 9/1996 | Hammond et al. | 435/6 |
| 5,596,401 A | 1/1997 | Kusuzawa | 356/23 |
| 5,601,235 A | 2/1997 | Booker et al. | 239/4 |
| 5,602,039 A | 2/1997 | Van den Engh | 436/164 |
| 5,602,349 A | 2/1997 | Van den Engh | 73/864.85 |
| 5,641,457 A | 6/1997 | Vardanega et al. | 422/82.01 |
| 5,643,796 A | 7/1997 | Van den Engh et al. | 436/50 |
| 5,650,847 A | 7/1997 | Maltsev et al. | 356/336 |
| 5,672,880 A | 9/1997 | Kain | 250/458.1 |
| 5,675,401 A | 10/1997 | Wangler et al. | 355/7 |
| 5,700,692 A | 12/1997 | Sweet | 436/50 |
| 5,707,808 A | 1/1998 | Roslaniec et al. | 435/6 |
| 5,726,364 A | 3/1998 | Van Den Engh | 73/864.85 |
| 5,759,767 A | 6/1998 | Lakowicz et al. | 435/4 |
| 5,777,732 A | 7/1998 | Hanninen et al. | 356/318 |
| 5,786,560 A | 7/1998 | Tatah et al. | 219/121.77 |
| 5,796,112 A | 8/1998 | Ichie | 250/458.1 |
| 5,804,143 A * | 9/1998 | Leary et al. | 422/73 |
| 5,815,262 A | 9/1998 | Schrof et al. | 356/318 |
| 5,835,262 A | 11/1998 | Iketaki et al. | 359/352 |
| 5,880,457 A | 3/1999 | Tomiyama et al. | 250/207 |
| 5,912,257 A | 6/1999 | Prasad et al. | 514/356 |
| 6,248,590 B1 * | 6/2001 | Malachowski | 436/63 |
| 6,275,777 B1 * | 8/2001 | Shimizu | 702/30 |
| 6,411,904 B1 * | 6/2002 | Chandler | 702/21 |
| 6,592,822 B1 * | 7/2003 | Chandler | 422/82.05 |

FOREIGN PATENT DOCUMENTS

| Country | Number | Date |
|---|---|---|
| DE | 0781985 A2 | 7/1997 |
| EP | 025296 A2 | 3/1981 |
| EP | 0160201 A2 | 11/1985 |
| EP | 0468100 A1 | 1/1992 |
| FR | 2699678 A1 | 12/1992 |
| JP | 61139747 (A) | 6/1986 |
| JP | 61159135 (A) | 7/1986 |
| JP | 2024535 | 1/1990 |
| JP | 4126064(A) * | 4/1992 |
| JP | 4126065(A) * | 4/1992 |
| JP | 4126066 (A) | 4/1992 |
| JP | 4126079(A) * | 4/1992 |
| JP | 4126080(A) * | 4/1992 |
| JP | 4126081 (A) | 4/1992 |
| RU | 1260778 A1 | 9/1986 |
| SU | 1056008 | 11/1983 |
| WO | WO 99/44037 | 2/1999 |

OTHER PUBLICATIONS

Ceruzzi, P., "History of Modern Computing", MIT Press, Reference to Non-von Neumann, 24 pages. no date.

Denk, W., et al (1995). Two-photon molecular excitation in laser scanning microscopy. Handbook of Biological Conical Microscopy. J.B. Pawley, ed., Plenum Press, New York. pp 444-448, no month.

Garner, D.L. et al; Quantification of the X- and Y- Chromosome-Bearing Spermatozoa of Domestic Animals by Flow Cytometry[1], Biology of Reproduction 28, pp. 312-321, (1983).

Johnson, Lawrence A. Sex Preselection by Flow Cytometric Separation of X and Y Chromosome-bearing Sperm based on NA Difference: a Review, Reprod. Fertil. Dev., 1995, 7, pp. 893-903.

Manni, Jeff; (1996). Two-Photon Excitation Expands The Capabilities of Laser-Scanning Microscopy, Biophotonics International, pp 44-52, no month.

Melamed et al, An Historical Review of the Development of Flow Cytometers and Sorters,, 1979, pp. 3-9, no month.

Piston, D.W., et al (1994). Two-photon-excitation fluorescence imaging of three-dimensional calcium ion activity, Applied Optics 33:662-669, no month.

Piston, D.W., et al. (1995), Three-dimensionally resolved NAD(P)H cellular metabolic redox imaging of the in-situ cornea with two-photon excitation laser scanning microscopy, J. of Microscopy 178:20-27, no month.

Radbruch, A Flow Cytometry and Cell Sorting, (Ed.), "Operation of a Flow Cytometer" by Gottlinger et al., 1992, no month, 8 pages, table of contents.

Shapiro, H. M.D., "Practical Flow Cytometry", Third Edition, John Wiley & Sons, Inc., Publication, 2 pages only, no date.

Skogen-Hagenson, M.J. et al; "A High Efficiency Flow Cytometer," The Journal of Histochemistry and Cytochemistry, vol. 25, No. 7, pp. 784-789, 1977, USA, no month.

Van Dilla et al. (Eds.), Flow Cytometry: Instrumentation and Data Analysis, "Flow Chambers and Sample Handling," by Pinkel et al., 1985, pp. 77-128, no month.

Van Dilla (Eds.)Flow Cytometry: Instrumentation and Data Analysis,, "Overview of Flow Cytometry: Instrumentation and Data Analysis" by Martin Van Dilla, 1985, pp. 1-8, no month.

Williams, R.M. et al. (1944). Two photon molecular excitation provides intrinsic 3-dimensional resolution for laser-based microscopy and microphotochemistry. FASEB J. 8: 804-813, no month.

"An Introduction to Flow Cytometry", pp 5-7 and pp 34-42 and p. 55, no date.

* cited by examiner

TRANSIENTLY DYNAMIC FLOW CYTOMETER ANALYSIS SYSTEM

This application is the United States National Stage of International application No. PCT/US00/41372 filed Oct. 20, 2000, which claims the benefit of U.S. Provisional application Ser. No. 60/160,719, filed Oct. 21, 1999, each hereby incorporated by reference.

This application makes reference to a Computer Program Listing Appendix submitted on two compact discs (which includes one duplicate copy), having the file name, "computerprogram.doc" containing 48 kb, all of which is hereby incorporated by reference herein. The compact discs were created on Aug. 25, 2004.

I. TECHNICAL FIELD

Specifically, flow cytometry apparatus and methods to process information incident to particles or cells entrained in a sheath fluid stream allowing assessment, differentiation, assignment, and separation of such particles or cells even at high rates of speed.

II. BACKGROUND

Flow cytometry is a field which has existed for many years. Basically, flow cytometer systems act to position small amounts of a substance within a sheath fluid. Through hydrodynamic focusing and laminar flow, the substance is split into individual particles, cells, or the like. In many applications, sheath fluid together with its entrained substance exits a nozzle in a jet and free falls or is channeled in an optically transparent pathway for analysis. The sheath fluid may form droplets encapsulating individual particles which are separated and collected based upon assignment of differentiated particle characteristics.

This type of analysis requires uniform conditions within the jet, very precise timing, and consistent comparative parameters incident to the entrained substances to separate such substances accurately. In addition, there is a coincident commercial and public sector demand for higher speed flow cytometry, the need to differentiate substances based on more complex and multiple parameter analysis, and for higher purity separation(s). Unfortunately, variation in equipment operation, sheath fluid stream dynamics, or observed particle characteristics still exists and are exacerbated by increasing the speed at which entrained substances are carried in the jet. As such, there is a need to compensate for such variations to provide for accurate analysis and separation of the substances entrained in the sheath fluid stream.

An overview of some attempts to understand and react to fluid stream and droplet dynamics can be seen in U.S. Pat. Nos. 4,317,520, 4,318,480, 4,318,481, 4,318,482, 4,318,483, and 4,325,483, each hereby incorporated by reference herein. As these explain, traditionally the approach has been to assess the signals and act directly upon such information. Some of the practical problems which have also been recognized is the fact that only a limited amount of space and time exists within which to conduct sensing and analysis. As Japanese Patent 2024535 also recognizes with respect to the sensing system alone, it may be desirable to have an optical system which is as small as possible.

As can be understood, a substantial problem can be that the data generated from an occurrence must be sensed and reacted upon in an extremely short period of time. Given the speed of microprocessors and the like, this might, at first glance, appear to be readily achievable. The challenge for this unique flow cytometry situation is that original or raw signal data can be sub-optimal and even unusable. As such, if it is to be used, it must be further processed in order to accomplish further analysis or decision making. This processing can be complex and can require more processing speed and power than is available not just with typical commercial systems, but even with today's highest-speed computer systems. Further, as the desire for higher processing frequencies is pursued, problems can be compounded. An example of the extremes to which speed has been taken is shown in U.S. Pat. No. 4,361,400, hereby incorporated by reference herein, where droplet formation frequencies in the range of 300 to 800 kilohertz had been achieved. Most practical droplet flow cytometers operate in the range of 10 to 50 kHz. Although speed of analysis problems have been known for years, prior to the present invention it has apparently been an accepted attitude that digital analysis in the flow cytometry context could not be achieved. This invention proves this expectation to be untrue. As a result of the present invention, droplet formation speeds in the 50–100–200 or higher kHz ranges are now possible with adequate data compensation and the like.

At any of these speeds, however, there appears to have been an expectation that analog analysis was the only practical way to achieve analysis of and to compensate for fluid dynamics, particle characteristics, equipment variance, and the like. To some degree, these expectations have been so prevalent that quality control, good manufacturing practices, regulatory approval, and other concerns have been set aside, diminished, or even compromised. The previously existing technology governing the practices of those in this field.

Another significant problem associated with conventional analysis and compensation of variables in flow cytometry can be the preservation of original signal data from an occurrence incident to the fluid stream prior to subsequent processing steps. It may not have been possible to preserve or store original signal data until now due to the short amount of time in which to analyze or compensate the original signal. As such, all or part of the original or raw signal data may have been sacrificed to increase the efficiency of analysis or provide feed back compensation events. The practice of discarding original raw data may prevent re-analysis of the data to improve quality control, to establish good manufacturing practices, and attain procedural thresholds for certain regulatory or statutory requirements.

Yet another problem with conventional analysis may be the inability to process high speed serial occurrences, to compensate multiple parameters, to perform complex operations, to provide transformation compensation of original data, or to apply compensated parameters. Conventional analysis can be limited by the amount of information that can be processed and returned in between serial events which can occur at a rates of at least 10,000 per second.

A first aspect of this inability can be associated with the nature of conventional signal processors used with flow cytometry. Conventional flow cytometer signal processors, often because they are analog, are not capable of dealing with large amounts of signal information, cannot perform operations on low quality signal information, cannot practically accomplish complex transformation operations (such as those which use algebraic expressions or structure), or they perform only reflexive feed back operations rather than serial or multi-variant analysis followed by subsequent parameter compensation.

A second aspect of this inability can be associated with the infrastructure of conventional data handling. In part, conventional infrastructure may not deal with how the streams of information are allocated, aligned, and coordinated. Conventional processing of flow cytometer information from occurrences incident to the fluid stream are traditionally handled as isolated feedback loops. As such, it can become increasingly difficult to synchronize various aspects of flow cytometer operation as the number of feed back loops increases. Moreover, these feed back loops may be completely uncoupled. For example, stream parameters, such as droplet break off location, may be completely uncoupled from the differential analysis of and separation of particles within the fluid stream being compensated.

A third aspect of this inability may be lack of symmetry reduction in the application of transformed data. Again, analog analysis can prevent or minimize symmetry reduction in the complex analysis of serial occurrences or parallel multivariant analysis. The lack of symmetry reduction or the inability to apply symmetry reduction to analysis terms may increase execution time.

As mentioned above, there has been a long felt but unsatisfied need for apparatus and methods which permit complex signal transformation, and use of compensated parameters resulting from complex signal transformation, real time analysis using compensated parameters, or storage of original signal data generated incident to the fluid stream, instrument variance, or environmental variance. The present invention addresses each of the above-mentioned problems with a practical solution. To some extent, it is apparent that solutions have not been achieved because those skilled in the art seem to have taken a direction which was away from the technical direction pursued in the present invention. This may have been the result of the fact that those skilled in the art did not truly appreciate the nature of the problem or it may have been the result of the fact that those skilled in the art were misled by some of the presumptions and assumptions with respect to the type of systems which could be considered. The present invention uses digital signal processing (DSP) technology to structure information from occurrences incident to flow cytometer operation, and to perform complex transformation, compensation, or analysis operations to achieve this long sought goal.

III. DISCLOSURE OF THE INVENTION

The present invention discloses a flow cytometer having DSP technology to solve problems associated with high speed serial occurrences, or multiple parameter analysis of occurrences, or both individually or in combination. While specific examples are provided in the context of flow cytometry applications to illustrate the invention, this is not meant to limit the scope of the invention to that field or to applications within flow cytometry. As such, the invention may also have numerous applications in various fields, for example, detection of defects in products as disclosed by U.S. Pat. Nos. 4,074,809 and 4,501,366; field flow fractionation, liquid chromatography, or electrophoresis as disclosed by U.S. Pat. No. 5,503,994; computer tomography, gamma cameras, or time of flight instruments as disclosed by U.S. Pat. No. 5,880,457, each of the above-mentioned patents are hereby incorporated by reference herein. It should be understood that the basic concepts of the invention may be applied not only to the area of flow cytometry but may apply to each of the above mentioned fields, or to other fields where the detection and analysis of small differences in parameters, such as photo-generated signal between serial occurrences having high incident light flux, or serial occurrences generating data concerning multiple parameters, or occurrences that generate a high number of signals in a short period of time, may be necessary or desired. Moreover, it should be understood that the invention can be divided into a number of embodiments which may be combined in various permutations and combinations. Naturally, as a result of these several different and potentially independent aspects of the invention, the objects of the invention are quite varied.

One broad object of an embodiment of the invention can be to convert original signals incident to the environment, the instrument, or a fluid stream, including but not limited to analog signals, to digital signals. One aspect of this object of the invention can be to harmonize a plurality of different types of signals into a fresh digitized data stream for processing. Another aspect of this object of the invention be to convert otherwise low quality or unusable signal data into usable quality signal data. In this regard, the original signal could be associated with a characteristic or multiple characteristics of single particle, such as a cell, within a fluid stream. Alternately, the original signal could be associated with a characteristic or multiple characteristics of a series of particles within a fluid stream. As such, numerous signals may be generated from the sensing of simultaneous occurrences (parallel occurrences) or the sensing of discrete occurrences over time (serial occurrences) that represent one, two, or any number of additional parameters. The rate of occurrences sensed may vary between about 10,000 occurrences per second to about 800,000 occurrences per second or more. The occurrences may be, as examples, the change in fluid dynamics at the jet or nozzle, the variation in performance of the equipment itself (such as the change in the baseline electronic signal from a photomultiplier tube), or the variation in performance of equipment due to the change in external conditions such as temperature or pressure. As to each, the occurrence, even when occurring at a high rate, or occurring for a limited duration, or occurring in a sub-optimal manner, may be sensed, converted to an original signal, and digitized.

Another broad object of an embodiment of the invention can be to perform compensation transformation on the original signal to provide compensated parameters. One aspect of this object can be to apply compensation transformation to processed data from a first signal incident to a first occurrence and to then apply compensation transformation to processed data from at least one additional signal incident to one or more occurrences to compensate a parameter(s) shared by the first occurrence and by at least one additional occurrence. A second aspect of this object can be compensation of parameter(s) that share characteristic(s) so that "cross talk" can be eliminated or minimized. Elimination or minimization of cross talk provides an increased ability to differentiate a first occurrence from a second or more occurrence(s). Differentiated occurrences may then be assigned to a class, separated, and collected.

Another object of an embodiment of the invention is to provide hardware or software infrastructure to allocate, align, or coordinate data generated from the above-mentioned original signals. One aspect of this object can be to provide multiple signal processors that can operate in parallel to increase the capacity to process signal data. The instant invention can utilize at least two but could utilize many parallel signal processors. The parallel signal processors could be stand aside hardware, or hardware that can coupled together via ether-net or Internet connections. A second aspect of this object of the invention can be to allocate different functions to the various parallel signal processors so as to optimize processing speed. A third aspect of this object of the invention can be to use linear assemblers and register usage to enhance parallel operation of and to coordinate the specialized functions performed by at least two signal processors. A fourth aspect of this object can be to provide software which optimizes the use of parallel processing of digital code. A fifth aspect of this object of the invention can be to apply symmetry reduction to serial transformation operations to reduce processing execution time.

Another object of an embodiment of the invention can be to perform complex operations on the above-mentioned original signals. Complex operations can be operations that were not possible or were not practical prior to the invention due to the speed at which the operations have to be performed in serial or in parallel, the number of parameters involved, the utilization of algebraic expressions or structure, the use of complex numbers to define variables, or the like. Each of these aspects can be complex individually or complex in combination.

Another object of an embodiment of the invention can be to save the original signal in a memory element or memory storage element. One aspect of this object can be to save the original signal without altering the original quality or quantity of the original signal. This may be necessary or desirable for quality control concerns or to meet regulatory or statutory requirements. Another aspect of this object can be to duplicate the original signal for analysis during flow cytometer operation or to duplicate the signal for future re-analysis.

Another object of an embodiment of the invention can be to provide software to implement the various applications on DSP technology. A first aspect of this object can be to provide exemplary compensation transformation operations. This may include compensation transformation for two-way compensation, three-way compensation, and so on for higher order compensation sets. A second aspect of this object can be to provide exemplary compensation matrices and their various properties. A third aspect of this object can be to provide exemplary symmetry reduction in various aspects of the software notation. A fourth aspect can be to provide an exemplary program for the subtraction of pairs or groups of fluorescent signals in order to orthogonalize the color sensitivity of each signal.

Yet another object of an embodiment of the invention can be to provide analog to digital converter compensation of amplified photomultiplier tube (PMT) outputs. Since emission spectra of fluorescent antibody labels are broadband, they can overlap the passbands of up to eight photomultiplier filters. Therefore, a digitized PMT output from even one antibody label can contain the effects of as many as eight antibody labels. See Shapiro, "Practical Flow Cytometry", pp. 17–19, 163–166 (1995), hereby incorporated by reference herein. This feature allows color sensitivity to be orthogonalized for each signal, and specifically allows for the application in the context of a flow cytometer such as those sold under the trademark MOFLO®.

Yet another object of an embodiment of the invention can be to provide the ability to latch numerous parameters either simultaneously or interchangeably, and to specifically latch any of the maximum of sixty-four MOFLO® flow cytometers parameters as inputs.

Another object of an embodiment of the invention can be to provide cross beam time alignment in order to perform enhanced compensation between a pair of parameters. One aspect of this object can be to reduce the apparent inter-beam transition time to not more than 1 part in 3000 or to a compensated beam to beam "time jitter" of not more than one nanosecond, which appears to be beyond the practical capability of analog circuit design.

Another object of an embodiment of the invention can be to provide digital error compensation. Digital subtraction is attractive because it avoids the problems of signal alignment, however, major digitalization errors can occur. For example, when bright signals are compensated over a large dynamic range digitized errors, which can be visually discernable as a picket-fence coarseness of the compensated population, can occur. Digital error compensation can minimize these errors and hence improve the quality of the digital information.

Another object of an embodiment of the invention can be to provide log amplifier idealization. Typically log amplifiers vary from ideal logarithmic behavior throughout their entire range. For example, some log amplifiers have a 0.4 dB variance. That is, for any given input, the ratio of the output signal from a practical log amplifier over the value expected of a perfect logarithmic function is expressed in dB as:

$$\text{Error} = 0.4 \text{ dB} = 20 \log 10(V_{out}/V_{ideal})$$

Log amplifier idealization can provide values which more closely approximate the ideal amplifier.

Another object of an embodiment of the invention can be to provide off-loaded binning. The characteristics of, for example, populations of particles can be stored in the memory of an additional signal processor using binning transformations. The statistical characterization of these populations, such as mean, standard deviation, skewness and separation can be sent to a separate processor, thus off-loading this task and hence increasing the performance of the first processor and the separate processor.

Naturally, further independent objects of the invention are disclosed throughout other areas of the specification.

V. MODE(S) FOR CARRYING OUT THE INVENTION

Specifically, an enhanced flow cytometer utilizing DSP technology and methods to process raw or original signal information incident to various parameters during operation, including, but not limited to, environmental parameters, instrument parameters, or parameters incident to the particles or cells entrained in a sheath fluid stream allowing for complex assessment, differentiation, assignment, and separation of such particles or cells, even when the flow cytometer is operated at high speed. Generally, a data acquisition, data transformation, parameter compensation, and compensated parameter utilization system for the differentiation, assignment, and separation of multiple parallel or serial events that can be useful in numerous fields and applications.

In discussing these aspects of the invention some references may be made to MOFLO® (a trademark of Cytomation, Inc.) flow cytometer systems and SUMMIT® (also a trademark of Cytomation, Inc.) capabilities for such systems. Each of these systems represent state-of-the-art flow cytometry capabilities which are not only the fastest practical flow cytometer systems, but they also are well known to those of ordinary skill in the art.

Figure 1:
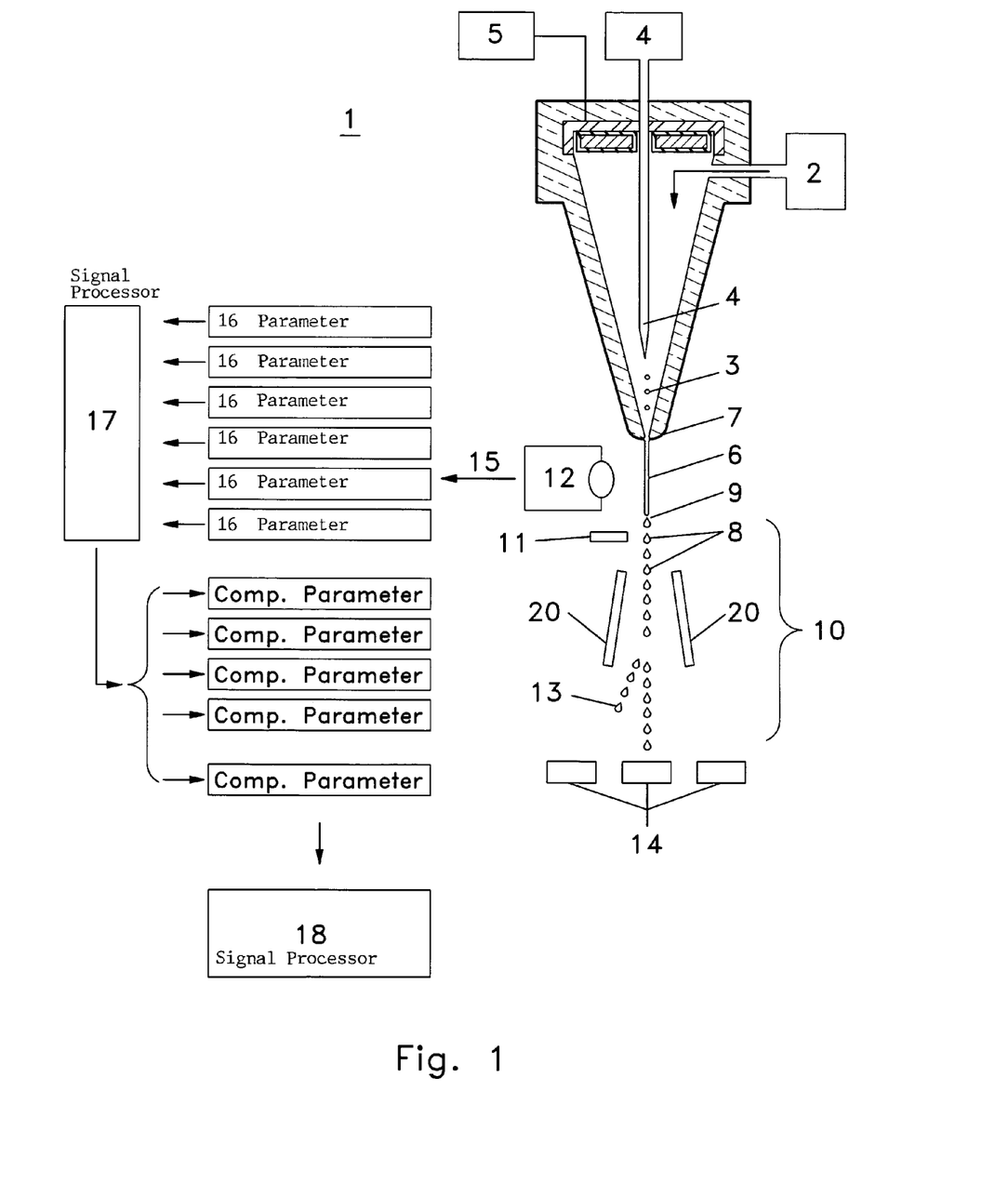
FIG. 1 shows a schematic cross sectional view of a flow cytometer embodiment of the invention showing the various features combined.

Referring now to FIG. 1, a preferred embodiment of the invention can be seen in detail. A flow cytometer (1) having a fluid stream source (2) can establish a fluid stream into which particles (3) can be suspended. The source of particles (4) can insert the particles from time to time such that at least one particle becomes suspended in and is hydrodynamically focused in the stream. An oscillator (5) responsive to the fluid stream perturbs the fluid stream. A jet or fluid stream (6) comprised of the fluid stream (2) and the particles (3) can then be established below the tip of the nozzle (7) of the flow cytometer. The stream can be established in a steady state condition such that droplets (8) that encapsulate a single particle form and break away from the contiguous part of the stream. When the stream is established in this steady state fashion, a stable droplet break-off point can be established. Below the droplet break-off point (9) a free fall zone (10) can exist. This free fall zone embodies the area where the droplets move once they break away from the contiguous part of the stream. A sensor (12), such as a laser and receiver in combination (or separately), can be used to monitor the stream for a particle. The sensor can sense an occurrence and generates a signal (15). For example, a coherent beam of light aimed at the fluid stream by the sensor (12) intercepts a particle (3) in the stream (6) and fluorescence or scattered light rays can then be emitted. The emitted fluorescence can be captured by the receiver, such as a photomultiplier tube, to generate the signal (15). Based upon analysis of the signal generated by the sensor from the fluorescent occurrence, the particle(s) may be differentiated, and assigned to a class. A droplet charging location (11) can exist at a point along the free fall zone. Based upon the assignment of the particle, the droplet can be charged positively, negatively, or left uncharged.

As the charged droplets fall in the free fall zone, they can pass through an electrostatic field (20). If the droplets have been charged with a positive or negative charge, an electric field established between these electrostatic plates can deflect the charged droplets such that the trajectory of the deflected droplets (13) and the trajectory of the neutral droplets serves to 20 separate one type of particle class from another. These separated particles can then be collected into a container(s) (14). Furthermore, alternative techniques such as utilizing different quantities of charge can be used to accomplish the assignment and separation of numerous classes of particles. The rate of separating the classes of particles or the sort rate can be at least 1000 per second.

The sensor (12) can be used to monitor or sense, and then assist in or generate a signal (15) incident to a variety of parameters (16) related to the operation of a flow cytometer or numerous other instruments (used individually or in combination). As described above, the raw or original signal(s) could be associated with a characteristic or multiple characteristics of a single particle (3), which could be a cell, entrained in the fluid stream (2). Alternately, the original signal could be associated with a characteristic or multiple characteristics of a series of particles (3) or cells within the fluid stream (2). As further mentioned above, numerous signals may be generated from the sensing of simultaneous occurrences (parallel occurrences) or the sensing of discrete occurrences over time (serial occurrences) that represent one, two, or any number of additional parameters (at least 64 parameters in the MOFLO® flow cytometer). The rate of occurrences sensed may vary between few per second or could be between about 10,000 occurrences per second to about 800,000 occurrences per second, or even higher. The original signal may also represent, as examples, the change in fluid dynamics at the jet or nozzle, the variation in performance of the equipment itself (such as the change in the baseline electronic signal from a photomultiplier tube), or the variation in performance of equipment due to the change in external conditions such as temperature or pressure. Specifically, as shown in FIG. 1 the parameters could be a variety of aspects incident to the fluorescent emission of fluorenyl isothiocyanate (FITC) upon excitation and include pulse width, forward scatter, side scatter, raw FITC information, raw PE (raw phycoerythrin), raw PE-CY5 (raw phycoerythrin CY5), and so forth. Naturally, numerous other parameters could be also be monitored and these specific examples are meant to be used as a guide rather than an inclusive list.

The MOFLO®, flow cytometer system, for example, monitors some conventional twelve bit parameters containing pulse width, analog to digital converter (ADC) channel outputs, timer outputs, Look Up Table (LUT) outputs, and the Classifier output. MOFLO®, flow cytometer system users can have need or desire to compute additional parameters which include compensating ADC outputs for the unwanted side effects of broadband fluorescence, computing ratios of ADC channel, and calculating whether ADC parameters fall inside, or outside 3D or higher dimensional regions, and the like. To expand the capability of instruments such as the MOFLO® flow cytometer system, other types of flow cytometer systems, or other types of instruments, the invention employs at least one additional signal processor (17) to apply compensation operations to the processed data from a first signal and to the processed data from a second or more signals. This may occur in parallel or simultaneous with the data processing of a first signal processor (18). The compensated output from the additional signal processor for at least one parameter shared by the signals (or the occurrences which generated the signals) allows enhanced differentiation between the first signal and the second signal based for the compensated parameter(s). The compensated data can then be combined into the data handling functions of the first signal processor, for example, and applied to classify and separate the occurrences.

Pass Through, Transformation and Return. Again referring to FIG. 1, and as mentioned above, the data emerging from the flow cytometer may exploit at least one additional signal processor, that can for example, be a parallel digital signal processor (17) which may be used simultaneously with a first signal processor. The original raw data or a portion of the original raw data from each signal generated by the flow cytometer can be assembled as a table of 32 or more 16 bit data words. The first 16 data words could be the raw data outputs from an occurrence, such as fluorescent emissions from excited fluorochromes used as surface or internal markers. The first 16 data words may be passed through the additional signal processor and the transformed output may be then presented on the second (or more) 16 data words. The final compensated parameters are returned to the first signal processor, combined with the output of the first signal processor, and then presented or displayed. This is often referred to as a pass-through and return digital signal path.

Naturally, the numeric data formats for a particular application may have to be matched. For example the raw 12 bit MOFLO® flow cytometer data can be thought of as a unsigned fixed point integers, in the format 12.0, that is 12 integer bits to the left of the fixed point, and 0 fractional bits to the right of the fixed point. This yields a range of 0x000

(0) to 0xFFF (4095). The compensated parameter output from the second signal processor (17) may need to be in the same format. The internal data manipulations can be changed as required, to perform the required algorithms. Possible internal data formats that could be used are 2's complement, signed integer, signed or unsigned fractional fixed point numbers, or floating point decimal, as examples. Various CPLD/FPGA (Complex Programmable Logic Devices/Field Programmable Gate Arrays) or digital signal processing Von Neuman or Harvard program, data, and I/O architectures may be used as required to perform algorithms. The algorithm and parameter coefficients for the compensated parameters may be changed during instrument operation. If desired, for example in the MOFLO® flow cytometer system, it should be able to be downloaded at operation time from the system's first computer, for example, through the MFIO Rev B Control Word Bus, using the same programming convention.

The additional signal processor(s) used in parallel can provide compensated parameters sufficiently fast that the data from numerous signals, channels, or parameters can have compensation transformation performed simultaneously. The speed of operation on the first group of 16 data words can occur before the second group of 16 data words becomes available. Each data word can pass through the additional signal processor at a rate of at least every 150 nanoseconds. Consequently, the additional signal processor can perform all operations to which it has been assigned for 16 data words within a maximum period of about 2410 nanoseconds.

As such, compensation transformation operations on the data from a signal(s) can provide compensated parameters to differentiate occurrences during flow cytometer operation. For such real time operation of a flow cytometer or other instrument, the additional signal processor(s) can perform compensation transformation operations for selected parameters even when the occurrences which are being differentiated have a rate of at least 10,000 per second or up to 800,000 occurrences per second. Naturally, the additional signal processor(s) could apply compensation transformation operations to occurrences having lower rates as well.

The compensated parameters generated by the additional signal processor(s) are then returned to the first signal processor. As such, the first signal processor can handle data for different tasks than the additional signal processors. In one embodiment of the invention, the first signal processor can perform the task of data management and display while the additional signal processors are performing, among other others, compensation transformation functions on the original signals. Thus, the separation of the tasks of data management and display and parameter compensation transformation may be an essential requirement to achieve accurate and reliable function.

As but one example of using the invention, with or without additional signal processor(s), compensation transformation, including complex operations, can be performed on the emission spectra of fluorescent antibody labels which overlaps the passbands of eight PMT filters. The compensation transformation operations can take the following form, and while this may be a preferred arrangement, a great variety of alternative embodiments are possible.

Two-way compensation:

Two linear signals from 0 to 1000 mV converted to a log signal in such a fashion that the log and linear voltages are related:

$$V^1\log=A.\log(V^1\lin/V_{th}) \quad (1)$$

$$V^2\log=A.\log(V^2\lin/V_{th}) \quad (2)$$

where $$A=10000/\log(10000/V_{th})$$

V/th is normally 1 millivolt. This formula ensures that an input from 1 millivolt to 10000 millivolts will produce a log signal from 0 to 10000 millivolts with 2.5 volts per decade.

A compensated parameter is a parameter with cross-talk subtracted out between two parameters. This is given by:

$$V^{1c}\lin=V^1\lin\,(1-C_{12})^{\wedge V^2\lin/V^1\lin} \quad (3)$$

$$V^{2c}\lin=V^2\lin\,(1-C_{21})^{\wedge V^1\lin/V^2\lin} \quad (4)$$

In order to recover the $V^1\lin$ and $V^2\lin$ from the log values, the inverse functions of (1) and (2) may be evaluated:

$$V^1\lin=V_{th}\exp(V^1\log/A) \quad (5)$$

$$V^2\lin=V_{th}\exp(V^2\log/A) \quad (6)$$

These linear values may be then applied to (3) and (4) above and converted to log by reapplication of (1) and (2).

In practice, this calculation will be performed on digital values whose linear range is 0 to 4095 (post digitization) and where the threshold value is 4095./10000.0.

Three-way compensation.

Mathematically this is the same process except that the formulae for the compensation set is:

$$V^{1c}\lin=V^1\lin(1-C_{12})^{\wedge V^2\lin/V^1\lin}(1-C_{13})^{\wedge V^3\lin/V^1\lin}\ldots \quad (7)$$

$$V^{2c}\lin=V^2\lin(1-C_{21})^{\wedge V^1\lin/V^2\lin}(1-C_{23})^{\wedge V^3\lin/V^2\lin}\ldots \quad (8)$$

$$V^{3c}\lin=V^3\lin(1-C_{31})^{\wedge V^1\lin/V^3\lin}(1-C_{32})^{\wedge V^2\lin/V^3\lin}\ldots \quad (9)$$

and so on for higher order compensation sets.

The lookup tables could be used for N-color compensation in the following way. Following this note on the transformation it is clear that N-color compensation can be deconstructed to N-12D lookups. For example, the 3-color compensated output when followed through from anti-log and back to log may look like this:

$$V^{1c}\log=V^1\log-\exp(V^2\log-V^1\log).\log(1-c_{12})-\exp(V^3\log-V^1\log).\log(1-c_{13})$$

Taking the first two terms together and the last term of this expression it is equivalent to:

$$V^{1c}\log=LUT(V^1\log,V^2\log)-LUT(V^1\log,V^3\log)$$

Applying the Transformation

The following notation convention is used to describe an "eight by eight" compensation matrix:

$p_{nc}$ where n=0 to 7 are the compensated outputs $p_n$ are the input log signals where n=0 to 7

$c_{jk}$ are the compensation coefficients=$-A^*\log(1-C_{jk})$ where $C_{jk}$ are the fractional compensation values ranging from $-0.999$ to $0.999$ $e(p_n-p_m)=\exp((p_n-p_m)/A)$ $A=4095.0/\log(10000)=444.6$ The compensation matrix may be as follows:

$$p_{oc} = p_{o-c01} \cdot e(p_{1-p0}) - c_{02} \cdot e(p_2-p_0) - c_{03} \cdot e(p_3-p_0) - c_{04} \cdot e(p_4-p_0) - c_{06} \cdot e(p_6-p_0) - c_{07} \cdot e(p_7-p_0) \quad (10)$$

$$p_{1c} = -c_{10} \cdot e(p_0-p_1) + p_1 - c_{12} \cdot e(p_2-p_1) - c_{13} \cdot e(p_3-p_1) - c_{14} \cdot e(p_4-p_1) - c_{15} e(p_{5-p1}) - c_{16} \cdot e(p_6-p_1) - c_{17} \cdot e(p_7-p_1) \quad (11)$$

$$p_{2c} = -c_{20} \cdot e(p_0-p_2) - c_{21} \cdot e(p_1-p_2) + p_2 - c_{23} \cdot e(p_3-p_2) - c_{24} \cdot e(p_4 p_2) - c_{25} \cdot e(p_5-p_2) - c_{26} \cdot e(p_6-p_2) - c_{27} \cdot e(p_7-p_2) \quad (12)$$

$$p_{3c} = -c_{30} \cdot e(p_{0-p3}) - c_{31} \cdot e(p_{1-p3}) - c_{32} \cdot e(p_2-p_3) + p_3 - c_{34} \cdot e(p_4-p_3) - c_{35} e(p_5-p_3) - c_{36} \cdot e(p_6-p_3) - c_{37} \cdot e(p_7-p_3) \quad (13)$$

$$p_{4c} = -c_{40} \cdot e(p_0-p_4) - c_{41} \cdot e(p_1-p_4) - c_{42} \cdot e(p_2-p_4) - c_{43} \cdot e(p_3-p_4) + p_4 - c_{45} e(p_5-p_4) - c_{46} \cdot e(p_6-p_4) - c_{47} \cdot e(p_7-p_4) \quad (14)$$

$$p_{5c} = -c_{50} \cdot e(p_0-p_5) - c_{51} \cdot e(p_1-p_5) - c_{52} \cdot e(p_2-p_5) - c_{53} \cdot e(p_3-p_5) - c_{54} e(p_4-p_5) + p_5 - c_{56} \cdot e(p_6-p_5) - c_{57} \cdot e(p_7-p_5) \quad (15)$$

$$p_{6c} = -c_{60} \cdot e(p_0-p_6) - c_{61} \cdot e(p_1-p_6) - c_{62} \cdot e(p_2-p_6) - c_{63} \cdot e(p_3-p_6) - c_{64} e(p_4-p_6) - c_{65} \cdot e(p_5-p_6) + p_6 - c_{67} \cdot e(p_7-p_6) \quad (16)$$

$$p_{7c} = -c_{70} \cdot e(p_{0-p7}) - c_{71} \cdot e(p_1-p_7) - c_{72} \cdot e(p_2-p_7) - c_{73} \cdot e(p_3-p_7) - c_{74} e(p_4-p_7) - c_{75} \cdot e(p_5-p_7) - c_{76} \cdot e(p_5-p_7) + p_7 \quad (17)$$

Note that the $c_{jk}$ are positive or negative and the parameters from which the others are subtracted are along the diagonal of the matrix.

Properties

There is symmetry around the diagonal in that the $e(p_j-p_k)$ terms one side of the diagonal are the inverse of those on the other. However this is not a useful symmetry since division is a time consuming operation on an integer arithmetic DSP device.

The functions $e(pj-pk)$ may range from $\exp(-4095/A)$ to $\exp(4095/A)$ since $p_n$ may be always positive and in the range 0 to 4095. This is a range from 1/10000 to 10000 which is an eight decade range. In order to do fast integer arithmetic, preferably the calculation of $e(p_j-p_k)$ should be done with a 16 bit map to preserve memory space, but the values in the lower ranges less than 1.0 are badly represented. This means that calculation accuracy cannot be maintained across all mapped values of $e(p_k-p_k)$.

It may be necessary to have two maps, one for positive and the other for negative arguments of $e(\ )$ in order to maintain accuracy.

Given these constraints, we can calculate the number of operations which may be needed to resolve this matrix.

|  | Operations | Speed (clocks) | Clocks |
|---|---|---|---|
| Pointer Loads | 4 | 4 | 16 |
|  | (2 maps, $p_n$ pointer, $c_{jk}$ pointer | | |
| Sum Initialization | 8 | 1 | 8 |
| Loads of $p_n$ | 8 | 4 | 32 |
| Subtracted Pairs | 28 | 1 | 28 |
| Mappings | 56 | 4 | 224 |
| Loads of $c_{jk}$ | 56 | 4 | 224 |
| Multiplies | 56 | 2 | 112 |
| Subtractions | 56 | 1 | 56 |
| Stores | 8 | 1 | 8 |
| Total | 280 | | 708 |

The 6201 DSP runs at a clock cycle of 5 ns. Thus, this calculation for non-optimized execution is 5*708=3540 ns. The MOFLO® flow cytometer system parameter bus runs at 150 ns per frame word, thus the number of MOFLO® flow cytometer system data words is:

3540/150=23.6

The last compensation parameter is in slot 10. The output needs to be ready at data word 16. The calculation matrix cannot be done as each MOFLO® flow cytometer system parameter comes across because the off-diagonal elements $e(p_j-p_k)$ may be mixtures of all parameters. The pipelining and parallel architecture of the DSP can allow substantial reduction of this calculation time.

Symmetry reductions can be made on this set in order to reduce execution time. The equations above can be multiplied by $e(p_n)$ and the diagonal terms moved to the left side $$(p_{0c}-p_0) \cdot e(p_0) = 0 - c_{01} \cdot e(p_1) - c_{02} \cdot e(p_2) - c_{03} \cdot e(p_3) - c_{04} \cdot e(p_4) - c_{05} \cdot e(p_5) - c_{06} \cdot e(p_6) - c_{07} \cdot e(p_7)$$

$$(p_{1c-p1}) \cdot e(p_1) = -c_{10} \cdot e(p_0) + 0 - c_{12} \cdot e(p_2) - c_{13} \cdot e(p_3) - c_{14} \cdot e(p_4) - c_{15} \cdot e(p_5) - c_{16} \cdot e(p_6) - c_{17} \cdot e(p_7)$$

$$(p_{2c}-p_2) \cdot e(p_2) = -c_{20} \cdot e(p_0) - c_{21} \cdot e(p_1) + 0 - c_{23} \cdot e(p_3) - c_{24} \cdot e(p_4) - c_{25} \cdot e(p_5) - c_{26} \cdot e(p_6) - c_{27} \cdot e(p_7)$$

$$(p_{3c}-p_3) \cdot e(p_3) = -c_{30} \cdot e(p_0) - c_{31} \cdot e(p_1) - c_{32} \cdot e(p_2) + 0 - c_{34} \cdot e(p_4) - c_{35} \cdot e(p_5) - c_{36} \cdot e(p_6) - c_{37} \cdot e(p_7)$$

$$(p_{4c}-p_4) \cdot e(p_4) = -c_{40} \cdot e(p_0) - c_{41} \cdot e(p_1) - c_{42} \cdot e(p_2) - c_{43} \cdot e(p_3) + 0 - c_{45} \cdot e(p_5) - c_{46} \cdot e(p_6) - c_{47} \cdot e(p_7)$$

$$(p_{5c}-p_5) \cdot e(p_5) = -c_{50} \cdot e(p_0) - c_{51} \cdot e(p_1) - c_{52} \cdot e(p_2) - c_{53} \cdot e(p_3) - c_{54} \cdot e(p_4) + 0 - c_{56} \cdot e(p_6) - c_{57} \cdot e(p_7)$$

$$(p_{6c}-p_6) \cdot e(p_6) = -c_{60} \cdot e(p_0) - c_{61} \cdot e(p_1) - c_{62} \cdot e(p_2) - c_{63} \cdot e(p_3) - c_{64} \cdot e(p_4) - c_{65} \cdot e(p_5) + 0 - c_{67} \cdot e(p_7)$$

$$(p_{7c}-p_7) \cdot e(p_7) = -c_{70} \cdot e(p_0) - c_{71} \cdot e(p_1) - c_{72} \cdot e(p_2) - c_{73} \cdot e(p_3) - c_{74} \cdot e(p_4) - c_{75} \cdot e(p_5) - c_{76} \cdot e(p_6) + 0$$

| Operation | Speed (clocks) | Clocks |
|---|---|---|
| Pointer loads | 4 | 2 | 8 |
| Sum initialization | 8 | 1 | 8 |
| Loads of pn | 8 | 4 | 32 |
| Mappings | 8 | 4 | 32 |
| Loads of $c_{jk}$ | 32 | 4 | 128 |
| Multiplies | 64 | 2 | 128 |
| Subtractions | 64 | 1 | 64 |
| Post NORM | 8 | 1 | 8 |
| Post SHL | 8 | 1 | 8 |
| Pointer loads | 2 | 2 | 4 |
| Post loads | 8 | 4 | 32 |
| Post remap | 8 | 4 | 32 |
| Post multiples | 8 | 2 | 16 |
| Post SHIFT ADD | 8 | 1 | 8 |
| Post SHR | 8 | 1 | 8 |
| Post adds | 8 | 1 | 8 |
| Stores | 8 | 1 | 8 |
| Total | | | 532 |

The execution time for this matrix is 2660 ns which is MOFLO® flow cytometer system frame words=2660/150=17.7 MOFLO® flow cytometer system data words.

Using the linear assembler and optimization of register usage to enhanced parallel operation can yield the parallel code set out in the Computer Program Listing Appendix. In the Computer Program Listing Appendix, the parallel bars are operations performed in one clock. The total number of clocks, ignoring the stack saving before and after which are imbedded to test the code from a C routine counts to 106 clocks or 540 ns. This gives the total MOFLO® flow cytometer system data words as 540/150 (150 is the time between MOFLO® flow cytometer system data words)=3.5 MOFLO® flow cytometer system data words.

This program, and the above-described example is not meant to limit the invention to specific hardware, software, algorithms, applications, or arrangements, but is provided as a guide in making and using the invention which may take the form of various embodiments. Particular embodiments of the invention, in the flow cytometry context or otherwise, can be as follows.

In certain applications, occurrences can be separated in time. Occurrences separated in time can be, in the flow cytometer context, for example, different original or raw signals generated for the same particle as it moves through the various flow cytometer processes which as above-described involve entrainment into a fluid stream, excitation of bound fluorochrome, assignment to a class, and separation of particles to the assigned classes. Occurrences separated in time can also involve a particle labeled with several different fluorochromes with each type of fluorochrome excited at different points in time. Again occurrences separated in time, could be a series of discrete occurrences each monitored for the same parameter, such as a fluorescent emission from a series of labeled cells, or it could be a single occurrence monitored at discrete periods in time, such as the characteristics of a fluorescent emission as it decays. Of course, numerous other examples could be provided which have occurrences separated in time. The spatial separation of these occurrences leads to original signal output which is separated in time. The use of additional signal processor(s) using pass through, compensation transformation, and return can remove this temporal separation. In some cases this will enable certain applications which were heretofore not possible, such as the use of multiple separate lasers to excite multiple fluorochromes over time, in other cases it will allow the original signals to have compensation transformation applied and more accurate differentiations made between occurrences even during operation of the instrument. Operations such as this which have a low tolerance for "time jitter" often cannot be performed using an analog arrangement because of the difficulty of removing the temporal separation with analog circuitry.

In certain applications "cross talk" between the same or different parameters can occur. Compensation transformation on the original or raw signals can remove "cross-talk" between the same or different parameters which are incident to the same or different occurrences. As described above, the "cross talk" between different types of fluorochrome emission was compensated. Compensation transformation may allow the raw original fluorescent signals, or numerous other types of signals, to be compensated so that the resulting compensated parameter has the cross-talk accurately removed and blank reference signals correctly positioned. This may be particularly relevant to other types of applications such as the detection of defects in products as disclosed by U.S. Pat. No. 4,074,809 and 4,501,366; field flow fractionation, liquid chromatography, or electrophoresis as disclosed by U.S. Pat. No. 5,503,994; computer tomography, gamma cameras, or time of flight instruments as disclosed by U.S. Pat. No. 5,880, 457; or flow cytometry as disclosed by U.S. Pat. No. 5,135,759 with respect to bright fluorescent values, each hereby incorporated by reference herein. This type of compensation transformation can be performed on numerous channels simultaneously, at least 8 channels in the above-described example, and provides orthogonalized data which can be returned to the first signal processor.

Certain applications require multiple color compensation. Compensation transformation for multiple color compensation can take the format presented above and allow for at least 8 color compensation embodied by a 64 element matrix of operations. The transformation can operate on linear or logarithmic format data. Naturally, as explained higher order set can be used providing for N-color compensation.

Certain applications require analysis of parameter kinetics or ratios. Ratios between two signals over time can be an important measurement in the study of cell kinetics. The original signals can be compensated such that the ratio can be used to provide a measure of absolute differences between the signals. For example, calcium release can be an important measurement for the study of cell kinetics. A ratio of two fluorescent emission signals can be required to provide a measure of calcium release. These fluorescent emission signals can have compensation transformation applied to provide compensated fluorescent emission signals for comparison in the appropriate time frame required to maintain accuracy. Multiple ratios can also be performed. Time can also be a parameter essential for kinetic measurements and can be supplied by the on-board clock. The on-board clock can have a time range from microseconds to years allowing full flexibility in time-stamping data streams.

Certain applications require differentiation of and tracking of sub-populations. Flow cytometers depend on the stability of various parameters, including, but not limited to, environmental parameters, instrument parameters, occurrence parameters to analyze and define the mean and width of particle populations. Unfortunately, these parameters can be in continuous dynamic instability. Stability can be controlled by compensation transformation of the original signals from these various parameters. Alternately, compensation transformation can track the drift in these parameters. Compensation transformation of original signal information can allow for the selection of parameters to resolve or differentiate sub-population, to select the level of resolution to be maintained between individuals of sub-populations, to select the thresholds for assignment and separation of individuals from sub-populations, to allow for continuous differentiation and assignment of individuals from sub-populations to various classes, to track sub-populations as parameters drift, to assess the purity of pools of separated individuals without re-analysis, among other applications.

In this regard, two dimensional, three dimensional, or higher dimensional populations of particles can be differentiated and assigned to various sub-populations and multi-dimension regions can be used to separate the sub-populations when using the invention. This provides a powerful and direct method of multi-dimensional sub-population separation that has been previously unavailable on flow cytometers, and on other types of instruments, and in other fields of application.

Another aspect, of sub-population identification involves closely overlapping sub-populations can be enumerated by dynamically characterizing the overlap using compensation transformations that may be designed to detect the proportion of overlaps. The exact proportions, mean, width and separation of multi-featured sub-populations can also be characterized with the invention. Extensive populations of particles with small sub-populations of interest can be focused upon and held in dynamic amplification or focus through transformation compensation of amplification parameters such that the sub-populations of interest can be defined, located, analyzed, and separated. Without transformation compensation, such accurate delineation may not be possible.

In applications using flow cytometry, particles with various population(s)/sub-populations of interest can be screened and regions of interest can be created which delineate these populations. These regions can be automatically assigned to the sorting electronics of a flow cytometer so that real-time physical separation of the particles of interest can be sorted. This automation process can be important when flow cytometry is used to separate high volumes of certain types of cells for culturing, transfecting, insemination, biochemical recombination, protein expression, or the like.

Populations of particles can be stored in the memory of the addition signal processor(s) using binning transformations. The statistical characterization of these populations, such as mean, standard deviation, skewness and separation can be returned to the first signal processor, that can be a workstation for display, storage, or retrieval of data. Thus off-loading this task to the additional signal processor can increase the performance of the workstation.

The method described above and detailed in the Computer Program Listing Appendix can preserve the raw signal data in a memory storage element. Cost considerations often exclude this feature on an analog systems. Saving raw or original signal data also conforms to Good Manufacturing Practice in that the original signal data can be retrieved if the transformed data has been incorrectly manipulated. By saving the original signal data and duplicating original signal data for further processing, elements ofthe original raw signal data that may be lost by digital 'roofing' or 'flooring' can be maintained. This can allow original signal retrieval and data backtracking for FDA requirements and for signal re-analysis.

Figure 2:
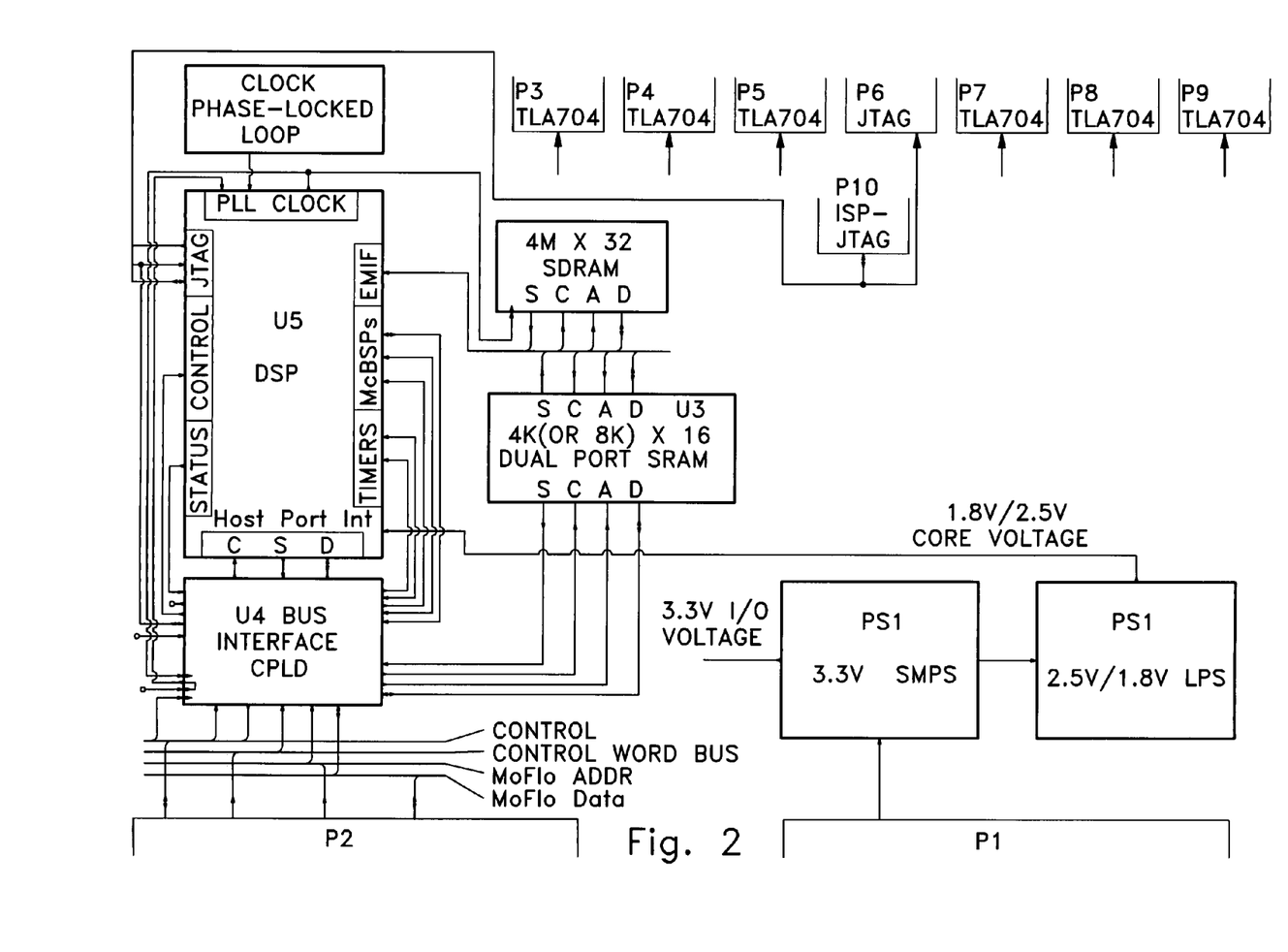
FIG. 2 shows hardware schematic of an embodiment of the invention.

Now referring to FIG. 2, a preferred embodiment of the hardware with respect to an application of the invention with the MOFLO® flow cytometer is shown. As can be understood, the additional signal processor (17) can be located internal to or external to the core of the instrument. A minimum data memory size of 56 kilowords of 12 bits or wider may be required for each compensation transformation operation (based on the example above). A minimum I/O memory space may also be required. Various CPLD/FPGA or digital signal processing Von Neuman and Harvard program, data, and I/O architectures, or the like, may be used to perform compensation transformation algorithms, such as those specified above.

Additional processors (17) serve to increase the parallelism of the operations, thus allowing transformations at hitherto unachievable speeds. This increased power allows operations that are algebraic as well as approximately transcendental. Transcendental operations can be considered those requiring an infinite number of steps. However extremely high processing rates can provide approximations to the infinite that are practicable and indistinguishable from an exact computation.

As can be easily understood from the foregoing, the basic concepts of the present invention may be embodied in a variety of ways. It involves both signal processing techniques as well as devices to accomplish the appropriate signal processing. In this application, the processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims which now be included.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action.

Similarly, each physical element disclosed should be understood to encompass a disclosure of the action which that physical element facilitates. Regarding this last aspect, as but one example, the disclosure of a "processor" should be understood to encompass disclosure ofthe act of "processing"—whether explicitly discussed or not—and, conversely, were there only disclosure of the act of "processing", such a disclosure should be understood to encompass disclosure of a "processor" and even a means for "processing". Such changes and alternative terms are to be understood to be explicitly included in the description.

Additionally, the various combinations and permutations of all elements or applications can be created and presented. All can be done to optimize the design or performance in a specific application.

Any patents, publications, or other references mentioned in this application for patent are hereby incorporated by reference. Specifically, U.S. Pat. application No. 60/160,719 is hereby incorporated by reference herein including any figures or attachments.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

The invention claimed is:

1. A method of flow cytometry, comprising the steps of:
    a. establishing a fluid stream;
    b. entraining particles in said fluid stream;
    c. perturbing said fluid stream;
    d. sensing a first occurrence incident to at least one particle;
    e. generating a first signal from said first occurrence incident to said at least one particle;
    f. producing data from said first signal;
    g. sensing at least one additional occurrence incident to said at least one particle;
    h. generating at least one additional signal from said at least one additional occurrence incident to said at least one particle;
    i. producing data from said at least one additional signal;
    j. processing data from said first signal;
    k processing data from said at least one additional signal;
    l. applying at least one transformation operation to processed data from said first signal;
    m. applying at least one transformation operation to processed data from said at least one additional signal;
    n. compensating at least one parameter shared by said first occurrence and said at least one additional occurrence;
    o. differentiating said first occurrence from said at least one additional occurrence based upon said at least one compensated parameter;
    p. assigning said at least one particle to a class;
    q. separating assigned particles; and
    r. collecting said assigned particles by class.

2. A method of flow cytometry as described in claim 1, wherein said steps of sensing a first occurrence incident to at least one particle and sensing at least one additional occurrence incident to said at least one particle comprise sensing occurrences incident to a single particle.

3. A method of flow cytometry as described in claim 2, wherein said step of sensing occurrences incident to a single particle comprises sensing serial occurrences.

4. A method of flow cytometry as described in claim 2, wherein said step of sensing occurrences incident to a single particle comprises sensing parallel occurrences.

5. A method of flow cytometry as described in claim 2, wherein said step of sensing occurrences incident to a single particle comprises sensing said occurrences incident to a same parameter.

6. A method of flow cytometry as described in claim 2, wherein said step of sensing occurrences incident to a single particle comprises sensing said occurrences incident to at least two parameters.

7. A method of flow cytometry as described in claim 1, wherein said steps of sensing a first occurrence incident to at least one particle and sensing at least one additional occurrence incident to said at least one particle comprise sensing occurrences incident to at least two particles.

8. A method of flow cytometry as described in claim 7, wherein said step of sensing occurrences incident to at least two particles comprises sensing serial occurrences.

9. A method of flow cytometry as described in claim 7, wherein said step of sensing occurrences incident to at least two particles comprises sensing parallel occurrences.

10. A method of flow cytometry as described in claim 7, wherein said step of sensing occurrences incident to at least two particles comprises sensing said occurrences incident to a same parameter.

11. A method of flow cytometry as described in claim 7, wherein said step of sensing occurrences incident to at least two particles comprises sensing said occurrences incident to at least two parameters.

12. A method of flow cytometry as described in claim 1, wherein said steps of producing data from said first signal and generating at least one additional signal comprise generating a single channel of information.

13. A method of flow cytometry as described in claim 1, wherein said steps of producing data from said first signal and generating at least one additional signal comprise generating multiple channels of information.

14. A method of flow cytometry as described in claim 1, wherein said steps of producing data from said first signal and generating at least one additional signal comprises generating said first signal and said at least one additional signal at a rate of 50,000 signals per second or greater.

15. A method of flow cytometry as described in claim 1, wherein said step of separating assigned particles comprises:
    encapsulating each one of said assigned particles in a droplet; and
    collecting said droplet encapsulating said each one of said assigned particles into a container.

16. A method of flow cytometry as described in claim 15, wherein said step of collecting said droplet encapsulating said each one of said assigned particles into a container occurs at a rate of at least 1000 per second.

17. A method of flow cytometry as described in claim 1, wherein said steps of applying at least one transformation operation to processed data from said first signal and applying at least one transformation operation to processed data from said at least one additional signal comprises performing complex operations on said processed data from said first signal and on said processed data from said at least one additional signal.

18. A method of flow cytometry as described in claim 17, wherein said step of performing complex operations on said processed data from said first signal and on said processed data from said at least one additional signal comprises performing algebraic operations.

19. A method of flow cytometry as described in claim 18, wherein performing algebraic operations comprises:
    applying a parameter compensation transformation to said first signal and to said at least one additional signal;
    generating a first compensated signal and at least one additional compensated signal; and
    comparing said first compensated signal and said at least one additional compensated signal.

20. A method of flow cytometry as described in claim 19, wherein said step of comparing said first compensated signal and said at least one additional compensated signal comprises minimizing characteristics shared by one parameter.

21. A method of flow cytometry as described in claim 20, wherein said step of minimizing characteristics shared by said one parameter comprises reducing spectrum overlap.

22. A method of flow cytometry as described in claim 21, wherein said step of minimizing characteristics shared by said one parameter comprises substantially aligning temporal serial events.

23. A method of flow cytometry as described in claim 19, wherein said step of comparing said first compensated signal and said at least one additional compensated signal comprises minimizing characteristics shared by at least two different parameters.

24. A method of flow cytometry as described in claim 23, wherein said step of minimizing characteristics shared by said at least two different parameters comprises reducing spectrum overlap.

25. A method of flow cytometry as described in claim 24, wherein said step of minimizing characteristics shared by said at least two different parameters comprises substantially aligning temporal serial events.

26. A method of flow cytometry as described in claim 1, further comprising the step of using a first signal processor and at least one additional signal processor in said steps of processing said data from said first signal and processing said data from said at least one additional signal.

27. A method of flow cytometry as described in claim 26, wherein said step of using a first signal processor and at least one additional signal processor comprises using said at least one additional signal processor in parallel with said first signal processor.

28. A method of flow cytometry as described in claim 27, wherein said step of using said at least one additional signal processor in parallel with said first signal processor comprises using said first signal processor and said at least one additional signal processor simultaneously.

29. A method of flow cytometry as described in claim 28, wherein said step of using said first signal processor and said at least one additional signal processor simultaneously comprises utilizing at least a portion of code by said first signal processor and said at least one additional signal processor.

30. A method of flow cytometry as described in claim 29, wherein said step of utilizing at least a portion of code by said first signal processor and said at least one additional signal processor comprises utilizing at least a portion of digital code by said first signal processor and said at least one additional signal processor.

31. A method of flow cytometry as described in claim 30, further comprising the step of applying a compensation matrix.

32. A method of flow cytometry as described in claim 31, further comprising the step of reducing execution time of applying said compensation matrix using compensation matrix symmetry reductions.

33. A method of flow cytometry as described in claim 1, further comprising the steps of:
saving original data from said first signal and said at least one additional signal in a memory storage element; and
retrieving said original data from said first signal and said at least one additional signal saved in said memory storage element without alteration.

34. A method of flow cytometry as described in claim 33, further comprising the steps of:
duplicating said original data from said first signal and said at least one additional signal to create a duplicate signal;
processing said duplicate signal;
interpreting said first occurrence and said at least one additional occurrence using said processed duplicate signal.

35. A method of flow cytometry as described in claim 34, further comprising the step of binning information in a signal processor.

36. A flow cytometer comprising:
a. a fluid stream;
b. at least one particle entrained in said fluid stream;
c. an oscillator responsive to said fluid stream;
d. a first sensor responsive to said at least one particle entrained in said fluid stream;
e. at least one signal generator;
f. data from said at least one signal generator incident to a first occurrence;
g. data from said at least one signal generator incident to at least one additional occurrence;
h. a signal processor of said data from said at least one signal generator;
i. a transformation operation applied to at least a portion of said data from said at least one signal generator incident to said first occurrence;
j. a transformation operation applied to at least a portion of said data from said at least one signal generator incident to said at least one additional occurrence;
k. a compensated parameter shared by said first occurrence and by said at least one additional occurrence;
l. a particle differentiation element configured to differentiate said first occurrence from said at least one additional occurrence;
n. a particle assignment element responsive to said particle differentiation element;
o. a particle separator based upon an assignment from said particle assignment element; and
p. at least one container in which separated particles are collected.

37. A flow cytometer as described in claim 36, wherein said transformation operation applied to at least a portion of said data from said at least one signal generator incident to said first occurrence and to said transformation operation applied to at least a portion of said data from said at least one signal generator incident to said at least one additional occurrence comprises a complex transformation operation.

38. A flow cytometer as described in claim 37, further comprising at least one additional signal processor.

39. A flow cytometer as described in claim 38, wherein said at least one additional signal processor performs said complex transformation operation applied to said at least a portion of said data from said at least one signal generator incident to said first occurrence and applied to at least a portion of said data from said at least one signal generator incident to said at least one additional occurrence.

40. A flow cytometer as described in claim 39, wherein said at least one additional signal processor is a digital signal processor.

41. A flow cytometer as described in claim 40, further comprising a memory element responsive to said digital signal processor, wherein said data from said at least one signal generator incident to said first occurrence and said data from said at least one signal generator incident to at least one additional occurrence is stored.

42. A flow cytometer as described in claim 41, further comprising an original data retrieval element.

43. A flow cytometer as described in claim 42, further comprising an original data duplication element.

44. A flow cytometer as described in claim 43, further comprising a binning element.

45. A method of flow cytometry, comprising the steps of:
a. establishing a fluid stream;
b. perturbing said fluid stream;

c. sensing an occurrence incident to said fluid stream;
d. generating a signal from said occurrence;
e. processing said signal using a first signal processor;
f. processing said signal using at least one additional signal processor in parallel with said first signal processor;
g. utilizing at least a portion of code by said first signal processor and said at least one additional signal processor;
h. combining output from said first signal processor and said at least one additional signal processor; and
i. applying said combined output to classify said occurrence.

46. A method of flow cytometry as described in claim 45, wherein said step of utilizing at least a portion of code by said first signal processor and said at least one additional signal processor comprises utilizing at least a portion of digitized code by said first signal processor and said at least one additional signal processor.

47. A method of flow cytometry as described in claim 46, further comprising the steps of:
performing compensation transformation on said signal; and
generating a compensated signal.

48. A method of flow cytometry as described in claim 47, wherein said step of performing compensation transformation on said signal comprises compensating a single parameter.

49. A method of flow cytometry as described in claim 48, wherein said step of compensating a single parameter comprises compensating an analog signal.

50. A method of flow cytometry as described in claim 47, wherein said step of performing compensation transformation on said signal comprises minimizing variations selected from the group consisting of phase, and shape.

51. A method of flow cytometry as described in claim 47, wherein said step of performing compensation transformation on said signal comprises compensating at least two different parameters.

52. A method of flow cytometry as described in claim 51, wherein said step of compensating at least two different parameters comprises minimizing characteristics shared by said at least two different parameters.

53. A method of flow cytometry as described in claim 52, wherein said step of minimizing characteristics shared by said at least two different parameters comprises reducing spectrum overlap.

54. A method of flow cytometry as described in claim 47, wherein said step of performing compensation transformation comprises applying algebraic operations on said signal.

55. A method of flow cytometry as described in claim 54, further comprising applying a compensation matrix.

56. A method of flow cytometry as described in claim 55, further comprising the step of minimizing execution time of performing said compensation transformation on said signal by utilizing symmetry reductions in said compensation matrix.

57. A method of flow cytometry as described in claim 47, wherein said step of performing compensation transformation on said signal comprises performing said compensation transformation on a plurality of signals generated at a rate of 50,000 occurrences per second or greater.

58. A method of flow cytometry as described in claim 45, further comprising the step of binning information in said at least one additional signal processor.

59. A method of flow cytometry as described in claim 45, further comprising the steps of:
saving original data from said signal in a memory storage element; and
retrieving said original data from said signal saved in said memory storage element substantially without alteration.

60. A method of flow cytometry as described in claim 45, further comprising the steps of:
duplicating original data from said signal;
processing said duplicate signal of said original data; and
analyzing said occurrence using said processed duplicate signal.

61. A flow cytometer comprising:
a. a fluid stream;
b. a sensor responsive to an occurrence incident to said fluid stream;
c. at least one signal generator coupled to said sensor;
d. a first signal processor to perform operations on signal data from said at least one signal generator;
e. a second signal processor to perform operations on said signal data from said at least one signal generator;
f. compensated parameter output from said second signal processor returned to said first signal processor; and
g. a particle differentiation element responsive to said compensated parameter output.

62. A flow cytometer as described in 61, further comprising a particle assignment element responsive to said particle differentiation element;
a particle separator based upon an assignment from said particle assignment element; and
at least one container in which separated particles are collected.

63. A method of flow cytometry, comprising the steps of:
a. establishing a fluid stream;
b. generating a first signal incident to said fluid stream;
c. generating at least one additional signal incident to said fluid stream;
d. applying parameter compensation transformation to said first signal and to said at least one additional signal;
e generating a first compensated signal and at least one additional compensated signal;
f. comparing said first compensated signal and said at least one additional compensated signal; and
g. classifying occurrences based upon comparison of said first compensated signal and said at least one additional compensated signal.

64. A method of flow cytometry as described in 63, further comprising the step of applying a compensation matrix on an output from said parameter compensation transformation.

65. A method of flow cytometry as described in 64, further comprising the step of using symmetry reductions within said compensation matrix to reduce execution time.

66. A method of flow cytometry as described in 65, further comprising the step of digitizing said first signal and digitizing said at least one additional signal.

67. A method of flow cytometry as described in 66, further comprising the step of processing said first signal and processing said at least one additional signal using a first signal processor in parallel with at least one additional signal processor.

68. A method of flow cytometry as described in claim 67, wherein said step of using a first signal processor in parallel with at least one additional signal processor comprises processing at least a portion of said first signal using said first signal processor and said at least one additional signal processor simultaneously.

69. A method of flow cytometry as described in claim 68, wherein said step of processing at least a portion of said first signal using said first signal processor and said at least one additional signal processor simultaneously comprises registering usage of a parallel digital linear code.

70. A method of flow cytometry as described in any one of claims 63, 64, 65, 66, 67, 68, or 69, wherein said step of applying said parameter compensation transformation to said first signal and to said at least one additional signal comprises applying compensation transformation at a rate of least 10,000 transformations per second.

71. A method of flow cytometry as described in claim 67, 68 or 69, further comprising the step of binning information in said at least one additional signal processor.

72. A method of flow cytometry as described in claim 71, further comprising the steps of:
saving original data from said first signal and said at least one additional signal in a memory storage element; and
retrieving said original data from said first signal and said at least one additional signal saved in said memory storage element substantially without alteration.

73. A method of flow cytometry as described in claim 72, further comprising the steps of:
duplicating said original data from said first signal and said at least one additional signal to create a duplicate signal;
processing said duplicate signal; and
interpreting said occurrences using said processed duplicate signal.

74. A flow cytometer comprising:
a. a fluid stream;
b. a sensor responsive to an occurrence incident to said fluid stream;
c. at least one signal generator coupled to said sensor;
d. a first signal generated by said at least one signal generator;
e. at least one additional signal generated by said at least one signal generator;
f. a signal processor responsive to said first signal and to said at least one additional signal;
g. a transformation operation applied to said first signal and to said at least one additional signal to create compensated parameters;
h. a compensated parameter comparison element configured to compare said compensated parameters; and
i. a particle differentiation element responsive to said compensated parameter comparison element.

75. A method of flow cytometry, comprising the steps of:
a. establishing a fluid stream;
b. perturbing said fluid stream;
c. sensing serial occurrences incident to said fluid stream;
d. generating an analog signal corresponding to said serial occurrences;
e. performing compensation transformation on said analog signal corresponding to said serial occurrences; and
f. minimizing variations of said analog signal corresponding to said serial occurrences, wherein variations are selected from the group consisting of phase and shape.

76. A method of flow cytometry as described in claim 75, wherein said step of performing compensation transformation comprises minimizing shared characteristics.

77. A method of flow cytometry as described in claim 76, wherein said step of minimizing shared characteristics comprises reducing spectrum overlap.

78. A method of flow cytometry as described in claim 75, wherein said step of performing compensation transformation comprises substantially temporally aligning said serial occurrences.

79. A method of flow cytometry as described in claim 75, further comprising the step of applying a compensation matrix on said analog signal corresponding to said serial occurrences.

80. A method of flow cytometry as described in claim 79, further comprising the step of reducing execution time of applying said compensation matrix by using compensation matrix symmetry reductions.

81. A method of flow cytometry as described in claim 75, further comprising the step of processing said analog signal corresponding to said serial occurrences using a first signal processor and at least one additional signal processor.

82. A method of flow cytometry as described in claim 81, wherein said step of processing said analog signal corresponding to said serial occurrences using a first signal processor and at least one additional signal processor comprises using said at least one additional signal processor in parallel with said first signal processor.

83. A method of flow cytometry as described in claim 82, wherein said step of using said at least one additional signal processor in parallel with said first signal processor comprises using said first signal processor and said at least one additional signal processor simultaneously.

84. A method of flow cytometry as described in claim 83, wherein said step of using said first signal processor and said at least one additional signal processor simultaneously comprises registering usage of a parallel linear code.

85. A method of flow cytometry as described in claim 84, wherein said step of registering usage of a parallel linear code comprises registering usage of a digital parallel linear code.

86. A method of flow cytometry as described in claim 81, further comprising the steps of:
saving original data from a first signal and original data from at least one additional signal in a memory storage element; and
retrieving said original data from said first signal or said original data from said at least one additional signal saved in said memory storage element substantially without alteration.

87. A method of flow cytometry as described in claim 86, further comprising the steps of:
duplicating said original data from said first signal and said original data from said at least one additional signal;
processing said duplicate signal of said original data;
interpreting a first occurrence and at least one additional occurrence using said processed duplicate signal.

88. A method of flow cytometry as described in claim 87, further comprising the step of binning information in said at least one additional signal processor.

89. A method of flow cytometry, comprising the steps of:
a. establishing a fluid stream;
b. entraining a substance in said fluid stream;
c. perturbing said fluid stream;
d. sensing serial occurrences incident to said substance, wherein said serial occurrences have a rate of 50,000 per second or greater;
e. generating a signal from said serial occurrences;
f. digitizing said signal;
g. interpreting said serial occurrences using said digitized signal;

h. saving said digitized signal in a memory storage element; and i. duplicating said digitized signal saved in said memory storage element.

90. A method of flow cytometry as described in claim 89, further comprising the step of processing said duplicate digitized signal using a first signal processor.

91. A method of flow cytometry as described in claim 90, further comprising the step of processing said duplicate digitized signal using at least one additional signal processor.

92. A method of flow cytometry as described in claim 91, further comprising the steps of using said at least one additional signal processor in parallel with said first signal processor and processing at least a portion of said duplicate digitized signal using said first signal processor and said at least one additional signal processor simultaneously.

93. A method of flow cytometry as described in claim 92, wherein said step of processing at least a portion of said duplicate digitized signal using said first signal processor and said at least one additional signal processor simultaneously comprises registering usage of a parallel digitized linear code.

94. A method of flow cytometry as described in claim 93, further comprising the step of performing complex operations on said duplicate digitized signal.

95. A method of flow cytometry as described in claim 94, wherein said step of performing complex operations on said duplicate digitized signal comprises performing algebraic operations on said duplicate digitized signal.

96. A method of flow cytometry as described in claim 95, wherein said step of performing algebraic operations on said duplicate digitized signal comprises performing compensation transformation on said duplicate digitized signal.

97. A method of flow cytometry as described in claim 96, wherein said step of performing compensation transformation on said duplicate digitized signal comprises compensating a single parameter.

98. A method of flow cytometry as described in claim 97, wherein said step of compensating a single parameter comprises compensating a serial analog signal.

99. A method of flow cytometry as described in claim 98, wherein said step of compensating said serial analog signal comprises minimizing variations selected from the group consisting of phase, and shape.

100. A method of flow cytometry as described in claim 96, wherein said step of performing compensation transformation on said duplicate digitized signal comprises compensating at least two different parameters.

101. A method of flow cytometry as described in claim 100, wherein said step of compensating at least two different parameters comprises minimizing characteristics shared by said at least two different parameters.

102. A method of flow cytometry as described in claim 101, wherein said step of minimizing characteristics shared by said at least two different parameters comprises reducing spectrum overlap.

103. A method of flow cytometry as described in claim 102, further comprising the step of generating a compensated signal.

104. A method of flow cytometry as described in claim 103, further comprising the step of re-processing said duplicate digitized signal.

105. A method of flow cytometry as described in claim 103, further comprising the step of using said compensated signal to differentiate components of said substance.

106. A method of flow cytometry as described in claim 105, further comprising the step of classifying a differentiated component.

107. A method of flow cytometry as described in claim 106, further comprising the step of separating said differentiated component from said substance.

108. A method of flow cytometry as described in claim 107, wherein said step of separating said differentiated component from said substance comprises:
encapsulating said differentiated component in a droplet; and
collecting said droplets encapsulating said differentiated component into a container.

109. A method of flow cytometry as described in claim 108, wherein said step of collecting droplets encapsulating said differentiated component into a container occurs at a rate of at least 1000 per second.

110. A method of flow cytometry, comprising the steps of:
a. establishing a fluid stream;
b. sensing an occurrence incident to said fluid stream;
c. generating an original signal from said occurrence;
d. saving said original signal in a memory storage element;
e. duplicating said original signal;
f. processing said duplicate signal of said original signal;
g. interpreting said occurrence using said processed duplicate signal.

111. A method of flow cytometry as described in claim 110, further comprising the step of retrieving said original signal saved in said memory storage element substantially without alteration.

112. A method of flow cytometry as described in claim 111, further comprising the step of re-processing said duplicate signal.

113. A method of flow cytometry as described in claim 112, further comprising the step of re-processing said retrieved original signal.

114. A method of flow cytometry as described in claim 113, further comprising the step of entraining a substance in said fluid stream.

115. A method of flow cytometry as described in claim 114, wherein said step of processing said duplicate signal comprises using said processed duplicate signal to differentiate components of said substance.

116. A method of flow cytometry as described in claim 115, further comprising the step of classifying a differentiated component.

117. A method of flow cytometry as described in claim 116, further comprising the step of separating said differentiated component from said substance.

118. A method of flow cytometry as described in claim 117, wherein said step of separating said differentiated component from said substance comprises:
encapsulating said differentiated component in a droplet; and
collecting droplets encapsulating said differentiated component into a container.

119. A method of flow cytometry as described in claim 118, wherein said step of collecting droplets encapsulating said differentiated component into a container occurs at a rate of at least 1000 per second.

120. A method of flow cytometry as described in claim 110, wherein said step of sensing an occurrence incident to said fluid stream comprises sensing serial occurrences.

121. A method of flow cytometry as described in claim 120, wherein said serial occurrences have a rate of at least 50,000 per second or greater.

122. A method of flow cytometry as described in claim 110, wherein said step of sensing an occurrence incident to said fluid stream comprises sensing a plurality of parallel serial occurrences.

123. A method of flow cytometry as described in claim 110, further comprising the step of digitizing said original signal from said occurrence.

124. A method of flow cytometry as described in claim 123, further comprising the step of using a first signal processor and at least one additional signal processor to process at least a portion of a duplicate digitized signal.

125. A method of flow cytometry as described in claim 124, wherein said step of using a first signal processor and at least one additional signal processor to process at least a portion of a duplicate digitized signal comprises processing at least a portion of said duplicate digitized signal using said first signal processor and said at least one additional signal processor simultaneously.

126. A method of flow cytometry as described in claim 125, wherein said step of processing at least a portion of said duplicate digitized signal using said first signal processor and said at least one additional signal processor simultaneously comprises registering usage of a parallel digitized linear code.

127. A method of flow cytometry as described in claim 124, further comprising the step of performing complex operations on said duplicate digitized signal.

128. A method of flow cytometry as described in claim 127, wherein said step of performing complex operations on said duplicate digitized signal comprises performing algebraic operations on said duplicate digitized signal.

129. A method of flow cytometry as described in claim 128, wherein said step of performing algebraic operations on said duplicate digitized signal comprises performing compensation transformation on said duplicate digitized signal.

130. A method of flow cytometry as described in claim 129, wherein said step of performing compensation transformation on said duplicate digitized signal comprises compensating a single parameter.

131. A method of flow cytometry as described in claim 130, wherein said step of compensating a single parameter comprises compensating a serial digitized analog signal.

132. A method of flow cytometry as described in claim 131, wherein said step of compensating said serial digitized analog signal comprises minimizing variations selected from the group consisting of phase, and shape.

133. A method of flow cytometry as described in claim 129, wherein said step of performing compensation transformation on said duplicate digitized signal comprises compensating at least two different parameters.

134. A method of flow cytometry as described in claim 133, wherein said step of compensating at least two different parameters comprises minimizing characteristics shared by said at least two different parameters.

135. A method of flow cytometry as described in claim 134, wherein said step of minimizing characteristics shared by said at least two different parameters comprises reducing spectrum overlap.

136. A flow cytometer, comprising:
a. a fluid stream;
b. an occurrence incident to said fluid stream;
c. a sensor responsive to said occurrence incident to said fluid stream;
d. at least one signal generator coupled to said sensor;
e. signal data generated by said at least one signal generator;
f. a memory element to store said signal data;
g. a stored signal data retrieval element configured to retrieve said stored signal data from said memory element;
h. a stored signal duplicator configured to duplicate said stored signal data; and
i. at least one signal processor responsive to a duplicated signal from said stored signal duplicator.

* * * * *